(12) United States Patent
Saunders

(10) Patent No.: US 7,900,616 B2
(45) Date of Patent: Mar. 8, 2011

(54) EXHAUST GAS OXYGEN SENSOR MONITORING

(75) Inventor: Jonathan Saunders, Coventry (GB)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 12/292,217

(22) Filed: Nov. 13, 2008

(65) Prior Publication Data

US 2009/0182490 A1 Jul. 16, 2009

Related U.S. Application Data

(63) Continuation-in-part of application No. 12/000,390, filed on Dec. 12, 2007, now abandoned.

(51) Int. Cl.
*F02D 41/00* (2006.01)
(52) U.S. Cl. ....... 123/688; 123/690; 701/109; 73/114.73
(58) Field of Classification Search .................. 123/674, 123/688, 690, 693; 701/107.109, 114; 73/1.06, 73/114.73
See application file for complete search history.

(56) References Cited

U.S. PATENT DOCUMENTS

| | | | | |
|---|---|---|---|---|
| 4,151,739 A | * | 5/1979 | Breuer et al. ................... 73/1.06 |
| 4,177,787 A | * | 12/1979 | Hattori et al. ............. 123/198 D |
| 4,191,151 A | * | 3/1980 | Wanamaker ................... 123/694 |
| 4,232,643 A | * | 11/1980 | Leshner et al. ............... 123/435 |
| 4,241,710 A | * | 12/1980 | Peterson et al. ............. 123/680 |
| 4,819,601 A | * | 4/1989 | Harada et al. ................. 123/681 |
| 4,878,381 A | * | 11/1989 | Moser et al. ................ 73/114.73 |
| 4,887,576 A | * | 12/1989 | Inamoto et al. ............... 123/688 |
| 4,981,125 A | * | 1/1991 | Kato et al. ..................... 123/693 |
| 5,212,947 A | * | 5/1993 | Fujimoto et al. ................. 60/276 |
| 5,227,975 A | * | 7/1993 | Nakaniwa ...................... 701/103 |
| 5,335,539 A | * | 8/1994 | Sweppy et al. ............. 73/114.72 |
| 5,423,203 A | * | 6/1995 | Namiki et al. ................. 73/1.06 |
| 5,488,858 A | * | 2/1996 | Achleitner ................. 73/114.73 |
| 5,558,752 A | * | 9/1996 | Wang et al. .................... 204/401 |
| 5,672,817 A | * | 9/1997 | Sagisaka et al. ............ 73/114.72 |
| 5,781,878 A | * | 7/1998 | Mizoguchi et al. ........... 701/109 |
| 5,801,295 A | * | 9/1998 | Davey et al. .................... 73/1.06 |
| 5,875,628 A | * | 3/1999 | Mitsutani ........................ 60/276 |
| 5,945,597 A | * | 8/1999 | Poublon et al. ............ 73/114.75 |
| 6,131,446 A | * | 10/2000 | Schnaibel et al. .......... 73/114.73 |
| 6,287,453 B1 | * | 9/2001 | Rosel et al. .................... 205/783 |
| 6,439,038 B1 | * | 8/2002 | Rosel et al. ................. 73/114.73 |
| 6,588,251 B2 | * | 7/2003 | Zhang et al. .................. 73/23.32 |
| 6,957,562 B2 | * | 10/2005 | Anilovich et al. .............. 73/1.06 |
| 7,040,085 B2 | * | 5/2006 | Namiki ............................ 60/277 |
| 7,073,320 B2 | * | 7/2006 | Moritsugu et al. .............. 60/276 |
| 7,461,536 B2 | * | 12/2008 | Schnaibel et al. .............. 73/1.06 |
| 7,520,274 B2 | * | 4/2009 | Sawada et al. ................ 123/690 |

(Continued)

*Primary Examiner* — Thomas N Moulis
(74) *Attorney, Agent, or Firm* — Nixon & Vanderhye P.C.

(57) ABSTRACT

An internal combustion engine includes an exhaust system, an oxygen sensor in the exhaust system and a sensor malfunction monitor. The sensor malfunction monitor measures a rate of change of a signal from the sensor on detecting a turning point of the signal and detects a malfunction when a rate of change of the signal exceeds a threshold. Alternatively, the sensor malfunction monitor measures a response time interval starting from a point in time at which a diagnostic function begins to force an air-fuel ratio to change (e.g., from lean-to-rich or rich-to-lean) and ends at a point in time when a turning point of the signal is detected. The sensor malfunction monitor detects a malfunction when the delay time of the response time interval, or average delay time from a plurality of measured response time intervals, exceeds a time threshold.

53 Claims, 12 Drawing Sheets

U.S. PATENT DOCUMENTS

| | | | |
|---|---|---|---|
| 7,549,284 B2 * | 6/2009 | Iihoshi et al. | 60/285 |
| 7,574,905 B2 * | 8/2009 | Toya | 73/114.73 |
| 2004/0006420 A1 * | 1/2004 | Yasui et al. | 701/110 |
| 2005/0173265 A1 * | 8/2005 | Stahl | 205/783.5 |
| 2009/0138182 A1 * | 5/2009 | Bruhn et al. | 701/109 |

* cited by examiner

EXHAUST GAS OXYGEN SENSOR MONITORING

CROSS REFERENCE TO RELATED APPLICATIONS

This application is a continuation-in-part of U.S. application Ser. No. 12/000,390 filed Dec. 12, 2007, the content of which is hereby incorporated herein by reference in this application.

BACKGROUND

1. Field of the Invention

Example embodiments of this invention relate to detecting sensor faults.

2. Related Art

An example of a situation where the detection of sensor faults is needed is in the case of a sensor of an internal combustion engine. As emissions requirements become more stringent, it becomes more important to ensure that sensors that are used in the control of an internal combustion engine are working correctly.

For example, it is likely that a requirement of the California Air resources Board (CARB) will be the detection of asymmetric malfunctions (i.e. that primarily affect only the lean-to-rich response rate or rich-to-lean response rate) and symmetric malfunctions (i.e., that affect both the lean-to-rich and rich-to-lean response rates) of an oxygen sensor in the exhaust system of an internal combustion engine.

As another example, the CARB may likely require that a diagnostic function detect an amount of time that a sensor, such as a vehicle's primary universal heated exhaust gas oxygen (UHEGO) sensor, takes to respond to a change in air-fuel ratio that causes the vehicle's tailpipe emissions to exceed legislated limits. That is, the CARB may require that the sensor's response time to an air-fuel ratio change that causes non-conforming tailpipe emission levels not exceed a certain threshold amount of time.

There is a need to provide a robust approach to the monitoring of a sensor response to facilitate the meeting of such requirements.

SUMMARY

An aspect of example embodiments of the invention provide a sensor malfunction monitor for detecting a sensor malfunction. The sensor malfunction monitor is operable to determine a turning point of a signal from the sensor for determining a measurement timing for verifying the operation of the sensor.

A malfunction of the sensor can be determined when, for example, a rate of change of a signal from the sensor falls outside an acceptable range of values.

An engine management system for an internal combustion engine can be provided with such a sensor malfunction monitor for detecting an asymmetric malfunction manifested in, for example, the lambda signal output by an oxygen sensor in the exhaust system of the internal combustion engine.

An internal combustion engine system can include an internal combustion engine, an exhaust system, an oxygen sensor in the exhaust system and such a sensor malfunction monitor.

Another aspect of example embodiments of the invention provide a method of detecting a sensor malfunction. The method can include determining a turning point of a signal from the sensor to determine a measurement timing for verifying the operation of the sensor.

Another aspect of example embodiments of the invention is to provide a method and system of detecting sensor malfunction based on a measured response time interval that starts at the time a diagnostic function begins to force the engine's air-fuel ratio to change and ends at the time that a turning point of a signal from an engine sensor is determined. For example, a diagnostic function (dither command signal) initiates a step change in the engine's air-fuel ratio from lean-to-rich or rich-to-lean. The time interval from this initiation of forced fueling change (i.e., forced change in air-fuel ratio) and the recognition of a sensor signal turning point is measured. The time of this interval may be compared to a failure criteria to determine if the sensor provides a sufficient response (e.g., a sufficiently prompt response time) so that the vehicle's tailpipe emissions may be maintained within legislated limits. A diagnostic test may therefore be accomplished based on the measured response time from a forced change in air-fuel ratio introduced by the diagnostic function to a turning point detection of a signal from a sensor, such as a UHEGO sensor.

BRIEF DESCRIPTION OF THE FIGURES

Specific embodiments of the present invention will now be described by way of example only with reference to the accompanying drawings.

Figure 1:
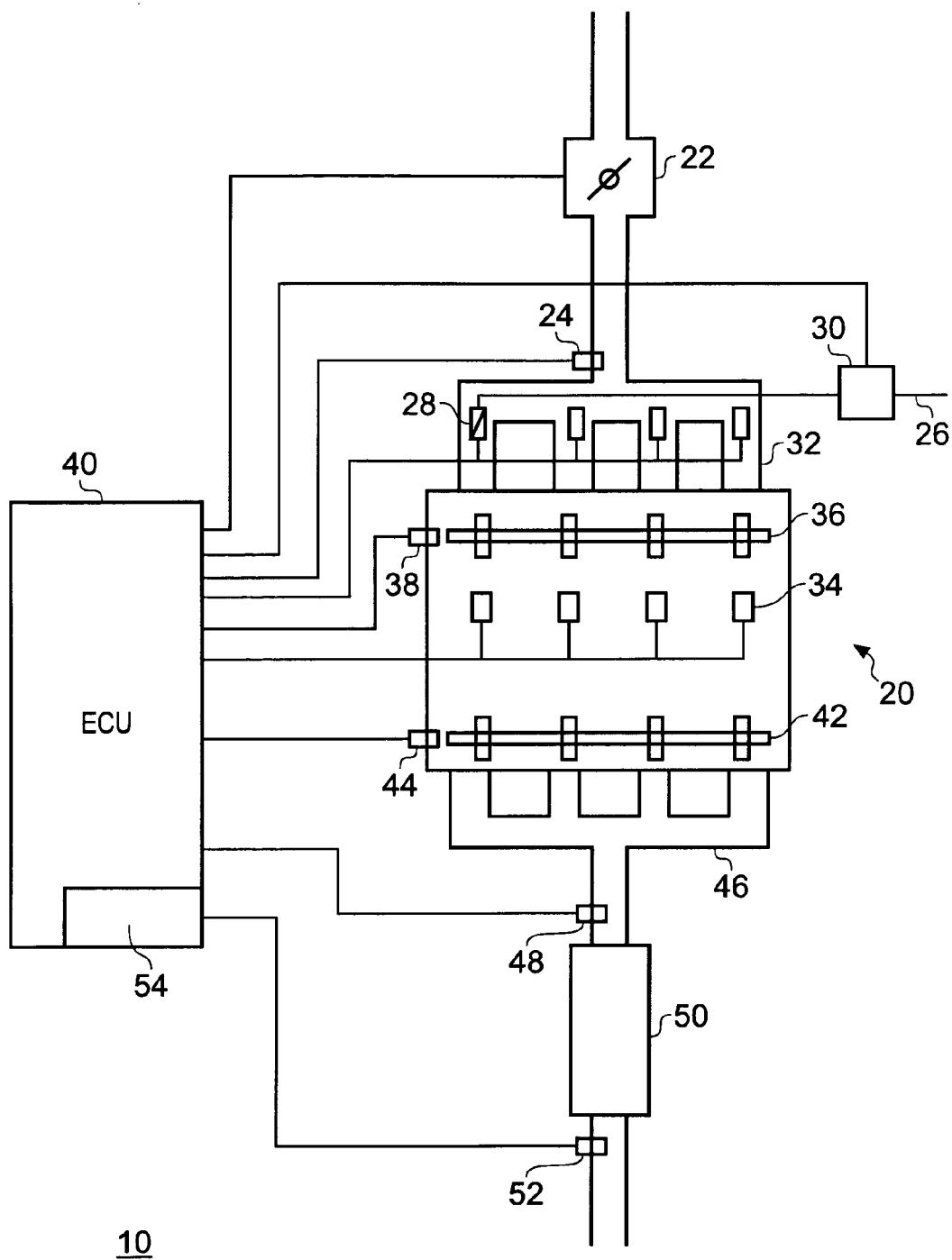
FIG. 1 is a schematic representation of an example of an internal combustion engine according to the present invention.

While the invention is susceptible to various modifications and alternative forms, specific embodiments are shown by way of example in the drawings and are herein described in detail. It should be understood, however, that drawings and detailed description thereto are not intended to limit the invention to the particular form disclosed, but on the contrary, the invention is to cover all modifications, equivalents and alternatives falling within the spirit and scope of the present invention as defined by the appended claims.

DETAILED DESCRIPTION

An embodiment of the invention can detect a sensor malfunction by analyzing a change in the signal output by a sensor in response to determining a turning point of the signal, whereby a malfunction of the sensor can be identified where the change of the signal falls outside given operating parameters. An example embodiment can form part of an engine management system for detecting a malfunction in an oxygen sensor in an exhaust system of an internal combustion engine.

FIG. 1 provides a schematic overview of an engine system 10 including an internal combustion engine 20. The internal combustion engine 20 represented in FIG. 1 is a four cylinder gasoline engine. The engine system is controlled by an engine control unit (ECU) 40 which is connected to various sensors and control subsystems of the engine system 10. The ECU 40 controls the operation of a throttle 22 at the intake side of the engine. A manifold pressure sensor 24 in an intake manifold 32 provides control signals to the ECU 40. A fuel injector 28 for each cylinder is connected to a fuel supply line 26. A pressure regulator 30 is used to control fuel pressure in the fuel supply line 26 and the individual injectors 28 receive control signals from the ECU 40 to control the timed injection of fuel. Spark plugs 34 receive ignition timing (IGT) signals from the ECU 40.

The engine control unit 40 receives signals from camshaft sensors 38 and 44 indicating the timing of the rotation of intake and exhaust camshafts 36 and 42, respectively. The intake and exhaust camshafts 36 and 42 respectively control intake and exhaust valves (not shown). The engine control unit receives other signals from other sensors (not shown) in a conventional manner such that the engine control unit is able to monitor operating parameters such as engine speed, engine load, etc. The engine control unit 40 also receives control signals from a universal heated exhaust gas oxygen (UHEGO) sensor 48 and a heated exhaust gas oxygen (HEGO) sensor 52. In the example shown the UHEGO sensor and the HEGO sensor are located either side of a catalytic converter 50, downstream of the exhaust manifold 46. However, in other examples, the positioning of UHEGO sensor 48 and/or the HEGO sensor 52 could be different. The engine control unit includes an oxygen sensor malfunction detection unit 54 that is described in more detail with respect to FIGS. 2 to 11.

Figure 2:
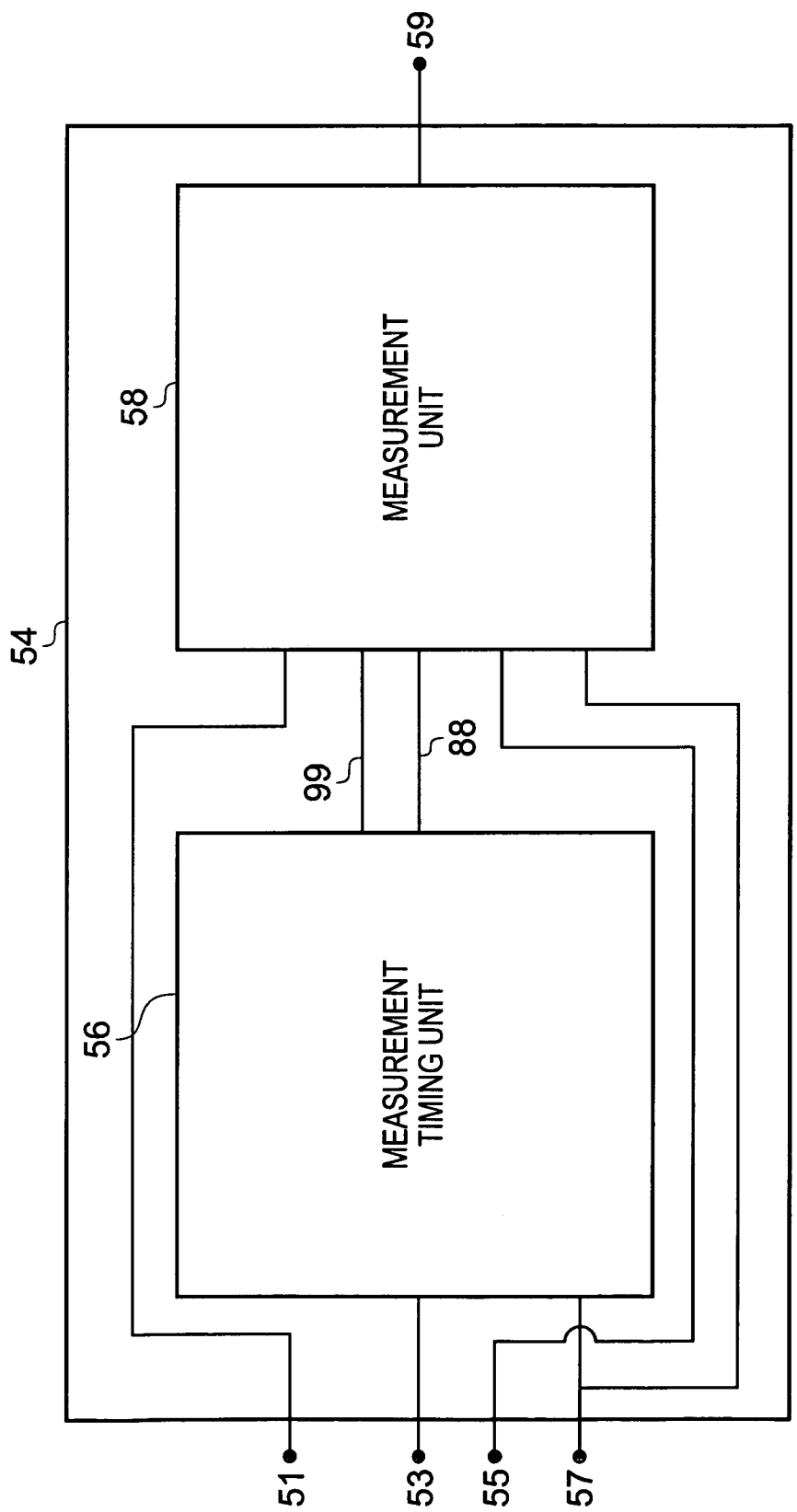
FIG. 2 is a block diagram of part of an example of an engine control unit for an example of embodiment of the invention.

FIG. 2 is a schematic overview of the oxygen sensor malfunction detection unit 54. The aim of the oxygen sensor malfunction detection unit 54 is to detect an asymmetric malfunction (i.e. that primarily affects only the lean-to-rich response rate or only the rich-to-lean response rate) and a symmetric malfunction (i.e., that affects both the lean-to-rich and the rich-to-lean response rates) of an oxygen sensor. The response rate can include delays in the sensor that initially react with the change in exhaust gas composition, as well as delays during the transition from a rich-to-lean or a lean-to-rich sensor output. In order to detect such malfunctions, it is necessary to determine appropriate measurement intervals. An example of the detection unit 54 illustrated in FIG. 2 provides for the detection of a measurement interval based on the detection of a turning of the output signal from the oxygen sensor being monitored.

In the example illustrated in FIG. 2, the oxygen sensor malfunction detection unit 54 includes measurement timing unit 56 and a measurement unit 58. The oxygen sensor malfunction detection unit is responsive to various signals including either raw or smoothed lambda signals 51 from the oxygen sensor (e.g. the UHEGO 48 or the HEGO 52—see FIG. 1) being monitored, a square wave timing dither signal 53 (see FIG. 9 later) that is used to control a target lambda signal, an engine speed parameter 55 (for example determined by the engine control unit 40 based on a crankshaft sensor) and engine load 57 (for example determined by the engine control unit 40 based on airflow sensors, pressure sensors, throttle sensors, etc. in a conventional manner. The oxygen sensor malfunction detection unit can output a fault signal 59, for example to trigger the engine control unit to illuminate the malfunction indicator light (MIL) in the vehicle. Also shown in FIG. 2 are timing signals 88 and 99 provided from the measurement timing unit 56 to the measurement unit 58 as will be described later.

Figure 3:
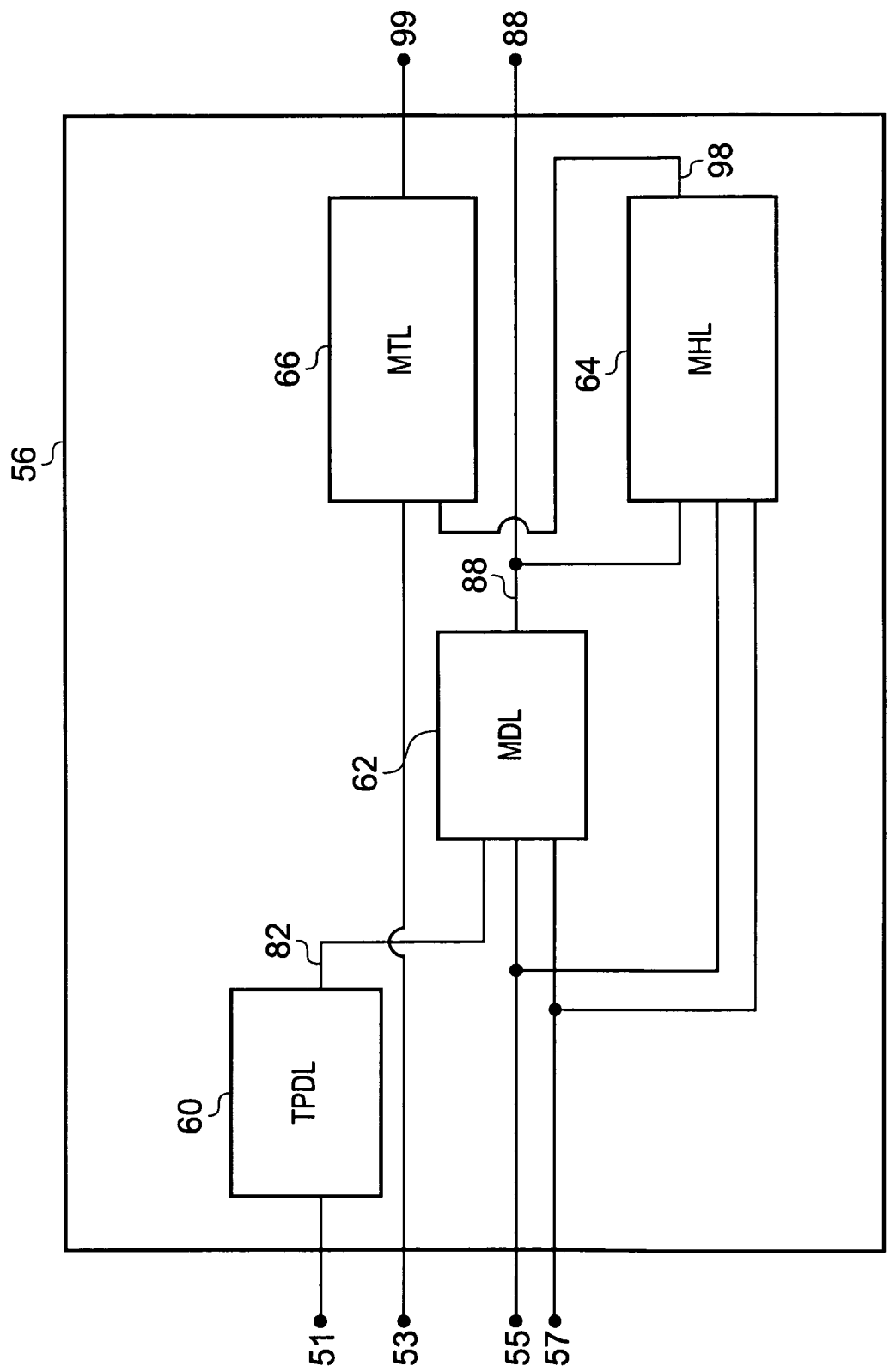
FIG. 3 is a schematic block diagram of an example measurement timing unit.

FIG. 3 is a schematic block diagram giving more detail of an example of measurement timing unit 56 that determines timings for measurements to be effected by the measurement unit 58.

Turning point detection logic (TPDL) 60 can be responsive to either the raw or smoothed lambda signals 51 from the oxygen sensor and is operable to determine a potential turning point by recognizing a rising or falling edge from two or more consecutive lambda samples in the same direction. A potential turning point signal 82 is output when the turning point logic detects a relationship between the lambda signals that is indicative of a turning point. The potential turning point signal 82 is supplied to measurement delay logic 62.

The measurement delay logic (MDL) 62 is operable to reset a delay timer each time a potential turning point signal 82 is received from the turning point detection logic 60, whereby a turning point is determined to have occurred when the timer times out. The measurement delay employed can be responsive to current engine operating conditions, and accordingly the measurement delay logic 62 can be responsive to engine parameters such as the engine speed parameter 55 and the engine load parameter 57. The measurement delay logic provides a determined turning point signal 88. The determined turning point signal 88 is supplied to the measurement logic 58 as indicated in FIG. 2. As will be explained later with reference to FIG. 9, the determined turning point signal 88 is operable to cause the measurement logic 58 to take a first lambda measurement.

Measurement hold logic (MHL) 64 is responsive to the determined turning point signal 88 and then holds the measurement time for a given response. The hold timing employed can be responsive to current engine operating conditions, and accordingly the measurement hold logic 64 can be responsive to engine parameters such as the engine speed parameter 55 and the engine load parameter 57. The measurement hold logic outputs a measurement trigger signal 98 which is provided to measurement termination logic 66.

The measurement termination logic (MTL) 66 is responsive to the dither signal 53 to the measurement trigger signal 98 and is operable to provide a measurement termination signal 99 that is supplied to the measurement logic 58 as indicated in FIG. 2. As will be explained later with reference to FIG. 9, the measurement termination signal 99 is operable to cause the measurement logic 58 to take a second lambda measurement.

Figure 4:
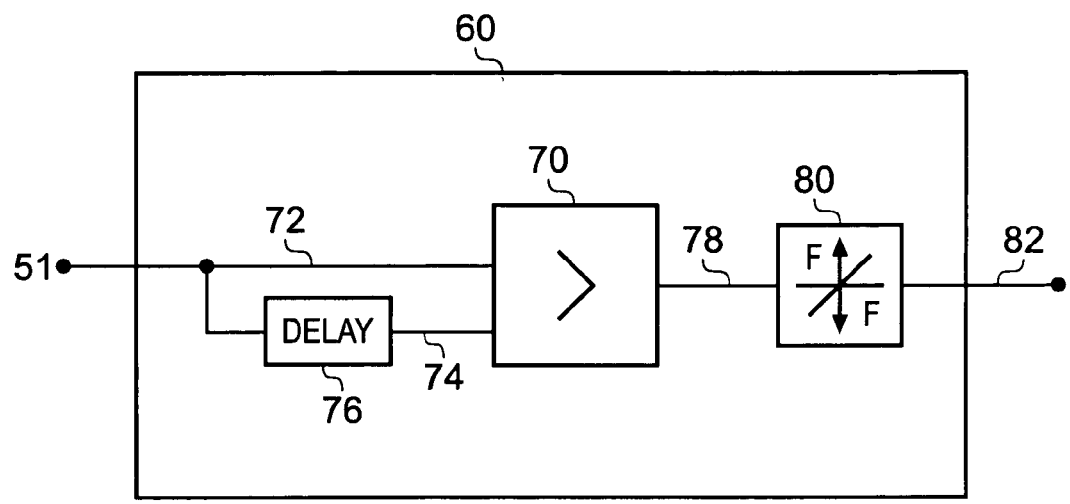
FIG. 4 is schematic block diagram of an example turning point detector.

FIG. 4 is a schematic representation of an example turning point detection logic 60. The turning point detection logic 60 can be responsive to the lambda signals 51 (either raw or smoothed lambda signals) from the oxygen sensor and can be operable to determine a potential turning point by recognizing a rising or falling edge from two or more consecutive lambda samples. Using smoothed lambda signals (rLmdSmth) as the lambda signals 51 can have the result that the signal/noise sensitivity for turning point determination is less dependent less on the measurement strategy and is more a matter of calibration. For example, using a series of successive consecutive sample checks, (e.g., six successive sample checks) accuracy can be improved. Measures can be under-taken to reduce the noise on the rLmdSmth signal 51 to facilitate the good judgment of a turning point.

In the example shown in FIG. 4, a given one (e.g., signal n) 72 of the lambda signals 51 can be compared in a comparator 70 to the preceding lambda signal (e.g., signal n−1) 74, which is delayed in a delay circuit 76. The output of the comparator 70 is a difference signal 78. The difference signal 78 can be in the form of a single bit where a first logical value (e.g., a 0 or 1) represents a positive difference representative of a rising signal and a second logical value (e.g., a 1 or 0) represents a negative difference representative of a falling signal. A zero difference between successive lambda signals can be represented by either the first logical value or the second logical value. A differential circuit 80 is connected to the comparator 70 and is operable detect a change in successive difference signals output by the comparator 70. A change in the logical value representative of change in the sign of the difference from a positive difference signal to a negative difference signal can be representative of a potential turning point where an increasing lambda signal changes to a decreasing lambda signal. A change in sign of the difference signal 78 from a negative difference signal to a positive difference signal can be representative of a turning point where a decreasing lambda signal changes to an increasing lambda signal. When the turning point logic detects a turning point, it outputs a potential turning point signal 82.

Where the lambda signal is fully smoothed, the turning point detection logic 60 can potentially enable a potential turning point of the lambda to be determined accurately.

However, more generally, and especially if there is noise on the lambda signal, detecting a single change in the difference signal 78 (effectively a change in the sign of the difference) may not be representative of the actual turning point.

To take account of this, as shown in FIG. 3, the potential turning point signal output from the turning point detection logic 60 is passed to the measurement delay logic 62.

Figure 5:
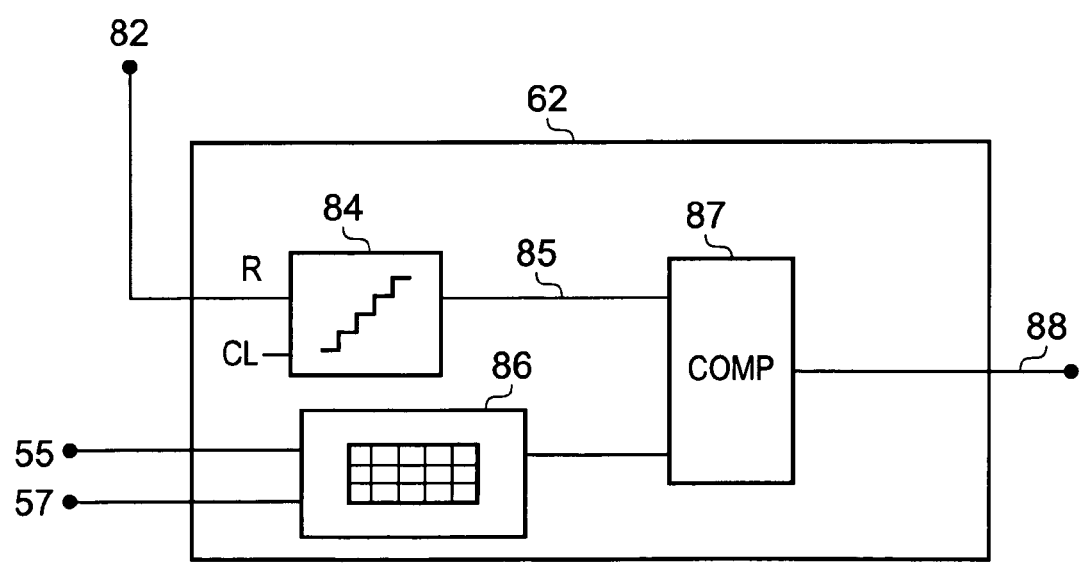
FIG. 5 is a schematic block diagram of example measurement delay logic.

FIG. 5 is a schematic representation of an example measurement delay logic 62. As illustrated in FIG. 5, a delay timer, or delay counter, 84 is reset each time a potential turning point signal 82 is received from the turning point detection logic 60. The delay counter 84 then counts (in response to a clock CL) until a threshold value is reached or another potential turning point signal is received, wherever occurs first.

The threshold value can be determined as a fixed counter value of the delay counter 84. However, in the example shown in FIG. 5, the threshold value is determined dynamically. A threshold value is determined from a threshold map 86 dependent on the current engine speed and engine load parameters 55, 57. The threshold value output from the threshold map 86 is compared in a comparator 87 to the output 85 of the delay counter 84 and, in the present instance the turning point is determined to be the timing when the counter value of the delay counter 84 reaches the threshold value. The determined turning point signal 88 is then output to the measurement hold logic 64.

It will be appreciated that in other examples, the determined turning point can be determined to have been reached when the counter value has an alternative relationship to the threshold value (e.g., when it exceeds the threshold value). Also, it will be appreciated that in other examples, the delay timer can be implemented as a count down timer, and/or the start value rather than the end value of the delay counter can be determined in a dynamic manner based on a value in a threshold map 86.

The measurement delay logic 62 can therefore allow for "noise" on the lambda signal, whereby the last of a series of noise spikes can be taken as the actual tuning point.

Figure 6:
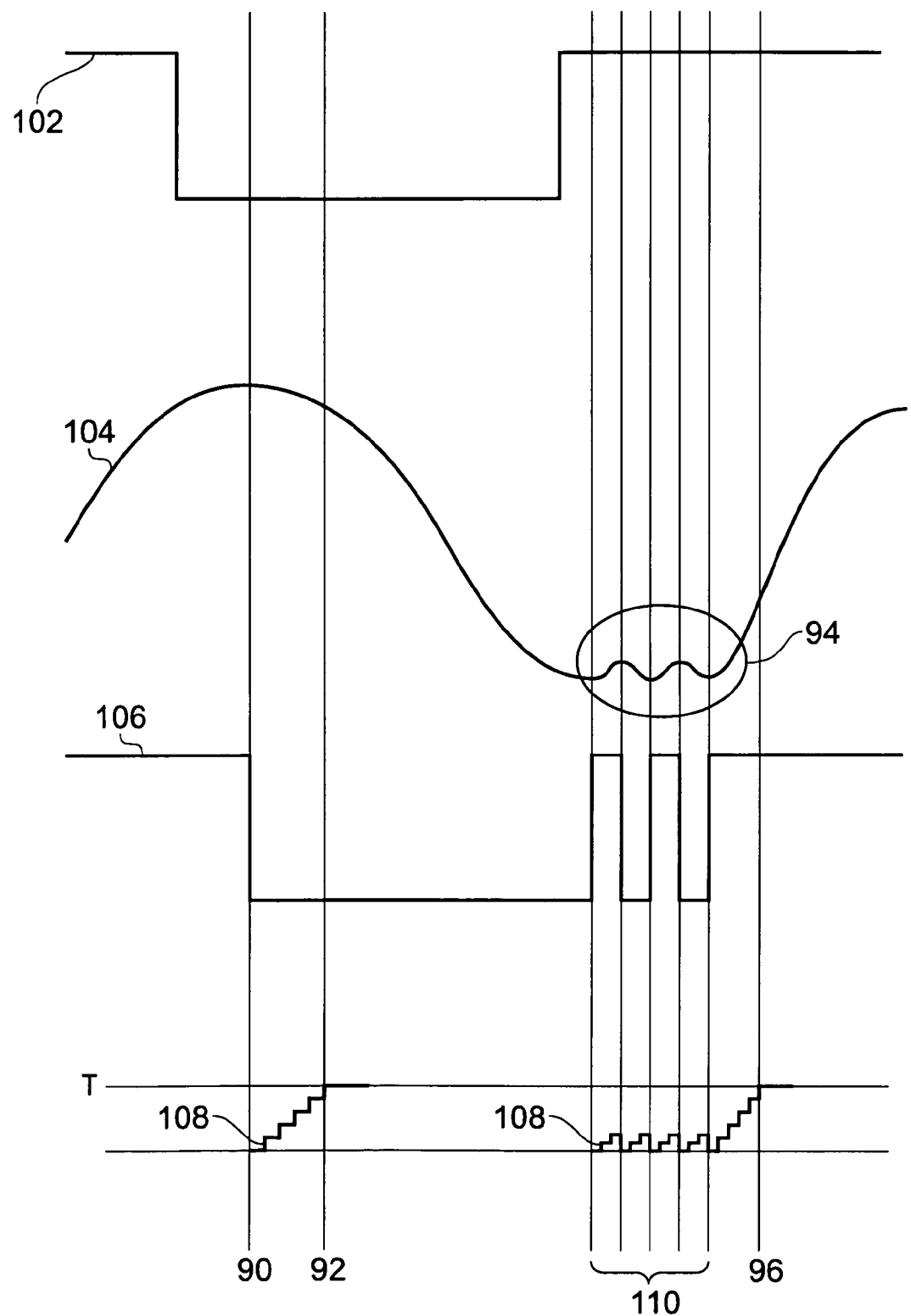
FIG. 6 is a diagram illustrating the operation of the measurement delay logic.

FIG. 6 illustrates this effect schematically, wherein trace 102 represents the dither signal mentioned earlier, trace 104 represents an example lambda signal, trace 106 is a trace recording changes in the difference signal 78 of FIG. 4 and trace 108 represents the output 85 of the delay counter 84. As illustrated in FIG. 6, a first potential turning point is detected by the turning point detection logic 60 (corresponding to the change in the difference signal in trace 106 at 90), and in response to the potential turning point signal 82 the delay counter is reset and starts counting at 90, whereby a first turning point is deemed to be detected at 92 when the delay counter reaches the threshold value T1. As also illustrated in FIG. 6, around the next turning point, there is noise 94 on the lambda signal 104. This has the result that around the turning point, the signal has a number of spikes that are detected by the turning point detection logic as a series of potential turning points. This results in a series of changes in the difference signal 78 (see trace 106). Each potential turning point signal 82 generated by the turning point logic 60 causes the delay counter 84 to be reset as represented at 110. The second turning point is determined at 96 when the delay counter reaches the threshold T1 following the last of the potential turning point signals 82.

Figure 7:
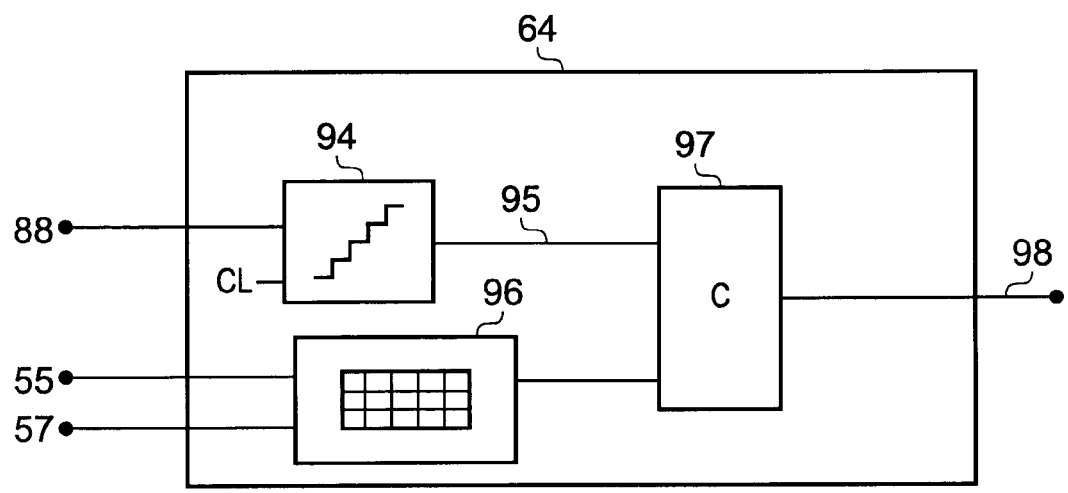
FIG. 7 is a schematic block diagram of example measurement hold logic.

FIG. 7 is a schematic representation of an example measurement hold logic 64 that is responsive to the determined turning point signal 88 to determine a hold timing from the determined turning point signal before issuing a trigger signal 98 to take a sensor measurement. As illustrated in FIG. 7, a hold timer, or hold counter, 94 is reset each time a determined turning point signal 88 is received from the measurement delay logic 62. The delay counter 94 then counts (in response to a clock CL) until a threshold value is reached.

The threshold value can be determined as a fixed counter value of the delay counter 94. However, in the example shown in FIG. 7, the threshold value is determined dynamically. A threshold value is determined from a threshold map 96 dependent on the current engine speed and engine load parameters 55, 57. The threshold value output from the threshold map 96 is compared in a comparator 97 to the output 95 of the hold counter 94 and, in the present instance the measurement trigger signal 98 is output when the counter value of the hold counter 94 reaches the threshold value. As described with reference to FIG. 5, although in the described example the counter used is a count up counter that times out at a dynamically adjustable upper limit, the starting point rather than the end point of the count could be adjusted dynamically and/or a count down timer could be used in other examples.

Figure 8:
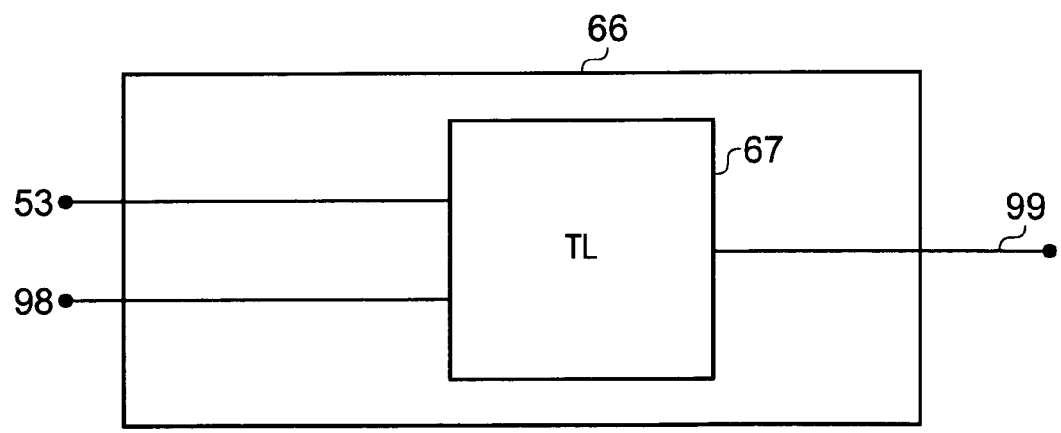
FIG. 8 is a schematic block diagram of example substitute timing logic.

FIG. 8 is a schematic block diagram of the measurement termination logic (MTL) 66. The measurement termination logic 66 includes timing logic 67 that is responsive to the first of a change in the dither signal 53 or receipt of the measurement trigger signal 98 to provide a measurement termination signal 99. The dither signal 53 is a signal used to determine a change in the target lambda signal (upwards or downwards) in accordance with engine operation conditions.

The measurement termination signal 99 is supplied to the measurement logic 58 as indicated in FIG. 2. The measurement trigger signal 98 from the measurement hold logic 64 could be supplied directly to the measurement logic 58 to cause a second lambda measurement to be taken. However, the provision of the measurement termination logic enables the trigger signal to be provided to the measurement logic 58 for taking a second lambda measurement even if the measurement time determined by the measurement hold logic (for example following a very noisy signal period) has not completed at the dither switch timing. This provides a counter measure for variable measurement starts during a fixed dither.

Figure 9:
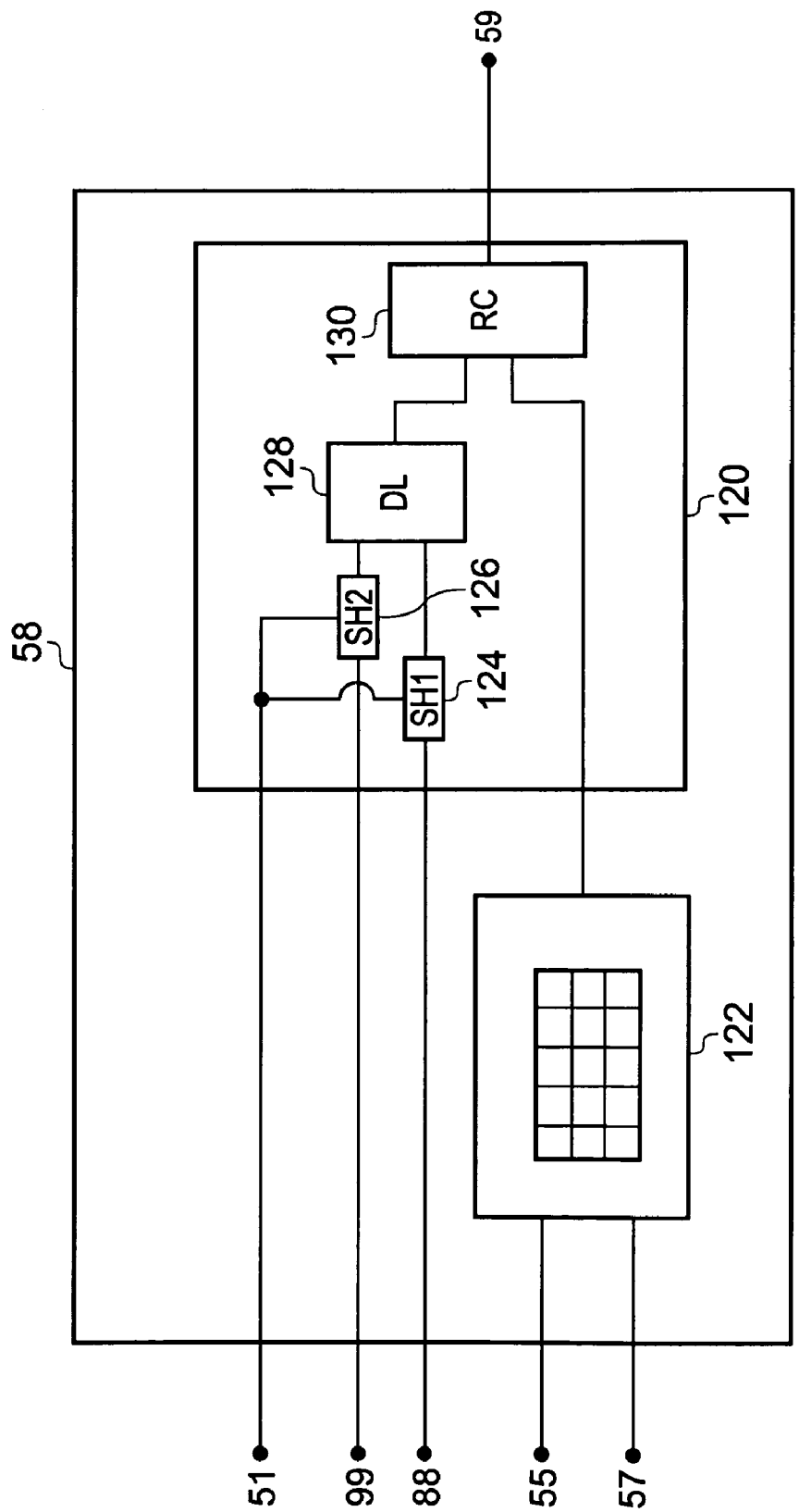
FIG. 9 is a schematic block diagram of an example measurement unit.

FIG. 9 is a schematic block diagram of the measurement unit 58 illustrated in FIG. 2. The measurement unit 58 comprises signal comparator logic 120 responsive to the determined turning point signal 88 and the measurement termination signal 99 to measure the lambda signal 51 at timings determined by the measurement and response signals. A first, reference, sample of the lambda signal 51 is taken by first sample and hold logic (SH1) 124 in response to the determined turning point signal 88 and a second, measurement, sample of the lambda signal 51 is taken by second sample and hold logic (SH2) 126 in response to the measurement termination signal 99. The sample and hold circuits can hold not only the sensed lambda values but also the timing of the samples. The rate of change of the lambda signal between the first and second samples lambda samples (that is between the reference and measurement samples) held in the first and second sample and hold logic 124 and 126, respectively, is computed in delta lambda logic 128 from the sample values and the timing of the samples.

The rate of change of the lambda signal computed by the delta lambda logic 128 is then compared by reference comparison logic 130 against rate of change reference values that define an acceptable rate of change range for the lambda signal output by the oxygen sensor. In the example shown in FIG. 9, the reference values used by the reference comparison logic 130 are provided from a signal map 122 that is responsive to engine operating parameters. In the example shown, the engine operating parameters used are current engine speed and engine load parameters 55, 57. It will be appreciated that in other examples fixed reference values could be used, or other engine operating parameters could be used to determine the reference values.

The reference comparison logic 130 is operable to determine whether the rate of change of the lambda signal computed by the delta lambda logic 128 falls inside or outside of the acceptable range of rate of change values for the oxygen sensor lambda signal as output from the signal map 122. Changes that fall within the range defined by the reference values are deemed to represent the correct functioning of the oxygen sensor. Changes that fall outside range defined by the reference values are deemed to represent a fault in the oxygen sensor and cause the reference comparison logic 130 to output a fault signal 59 that is passed to engine control unit logic responsible for illuminating the MIL.

As indicated above, in the example shown, the reference values define a range of acceptable rates of change of response of the oxygen sensor according to determined operating conditions. In other words, the parameters define a target delta (TgtDlt) for the response, and this is compared to the measured lambda delta (LmdDlt) for the measured response of the oxygen sensor. For example a too rapid or a too slow rate of change of the lambda signal from the oxygen sensor (e.g. a rate of change of the lambda signal that exceeds or falls below threshold values defined in the signal map 122) can both be indicative of a fault in the oxygen sensor.

Figure 10:
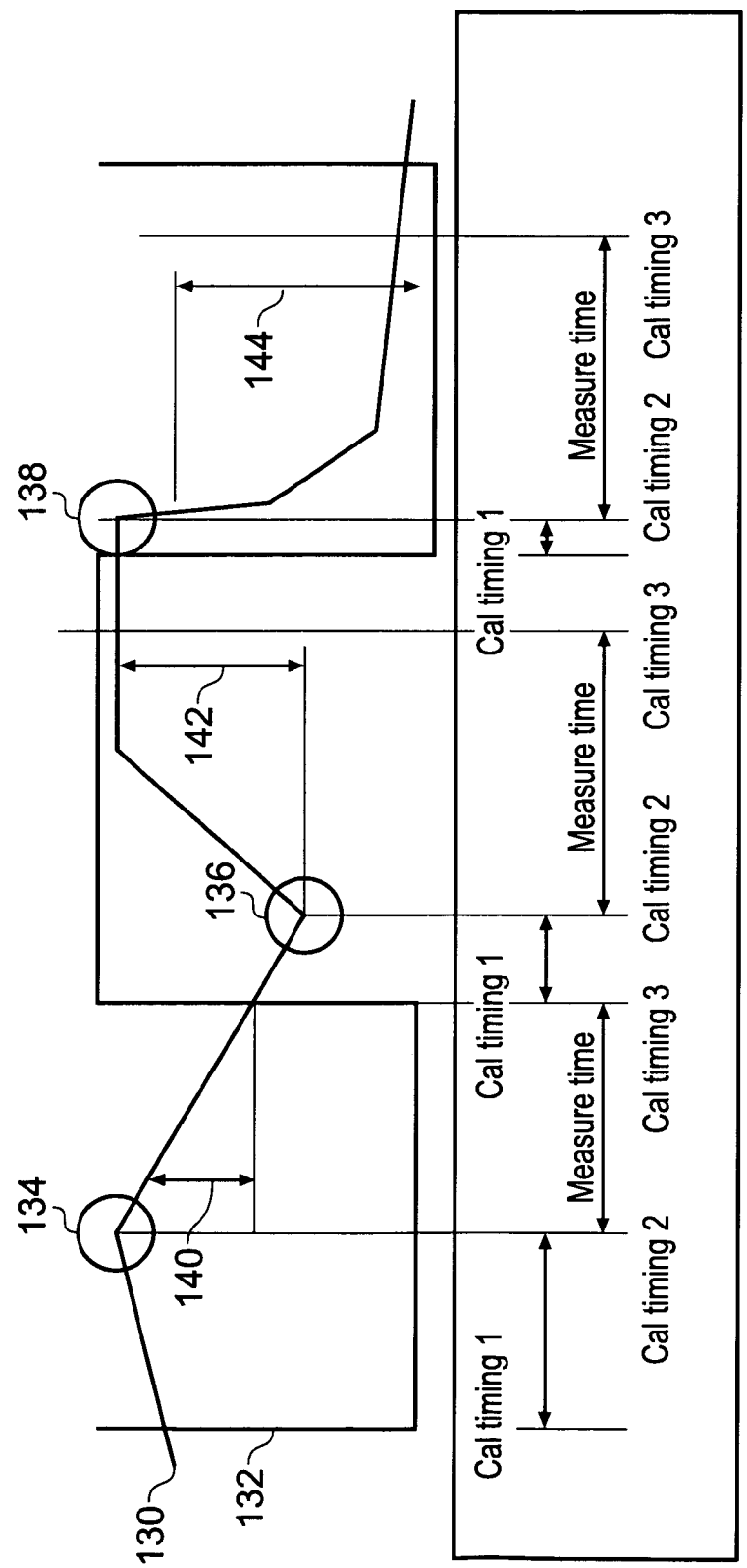
FIG. 10 is a diagram illustrating an example of turning point determination of an example embodiment of the invention.

FIG. 10 illustrates the effect of the oxygen sensor malfunction detection unit 54.

The trace 130 represents a smoothed lambda signal. The trace 132 represents a target lambda signal. The use of a measurement time starting from the turning point of the lambda signal, rather than a fixed timing, can automatically account for sensor conditions and engine operating conditions without further calculation. Accordingly, an example of an oxygen sensor malfunction detection unit such as the oxygen sensor malfunction detection unit 54 of FIG. 2 can enable the start time to be determined from the turning point of the lambda as shown, for example, at point 134, 136 and 138. As can be seen in FIG. 10 various measurement times can be initiated at those turning points. Thus, the turning point determination for calibration (cal) timing 2 illustrated in FIG. 10 can allow the delta of the lambda signal (LmdDlt) to be measured for the actual sensor response, which means that diagnosis is much more accurate for all sensors and operating conditions. In the example shown in FIG. 10, a bad response is correctly identified at 140 because the delta of the lambda (LmdDlt) is small. In comparison thereto, a good response is correctly identified at 142 and 144 because the delta of the lambda (LmdDlt) is large.

Figure 11:
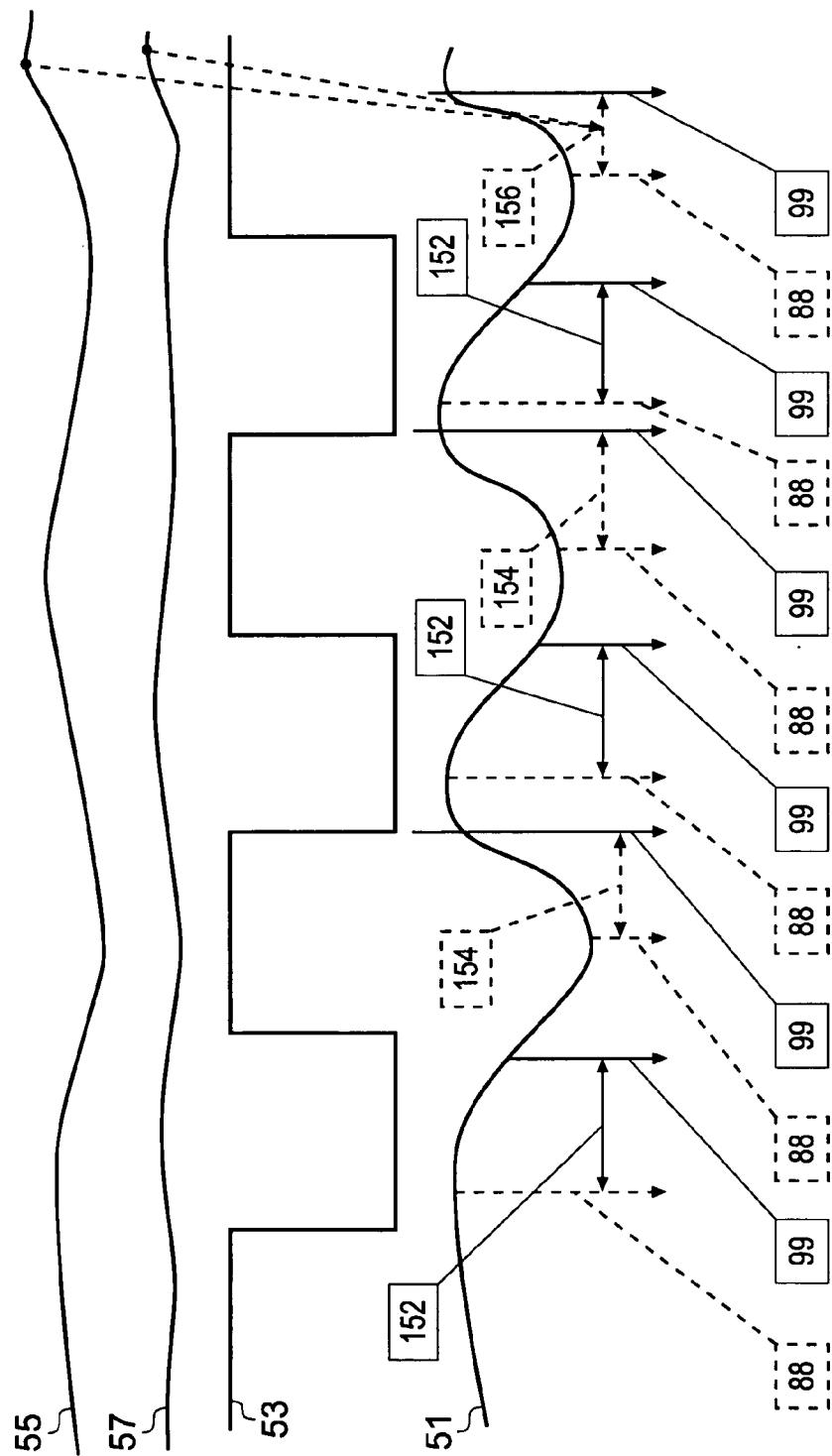
FIG. 11 represents the detection of lean-to-rich and rich-to-lean faults.

FIG. 11 illustrates an example of the effect of a strategy employed by an example of an oxygen sensor malfunction detection unit 54 in accordance with an embodiment of the invention.

FIG. 11 represents traces for engine speed 55, engine load 57, the target lambda resulting from the dither signal 53, and the measured, or a measured and smoothed, lambda signal 51.

In the example shown in FIG. 11, the delay from a turning point (defined by the determined turning point signal 88) to termination of the measurement (defined by the measurement turning point signal 99) can vary according to operating conditions. Different examples of this are shown in FIG. 11. The measurements labeled 152 represent measurement timings where a measurement is terminated in response to a measurement termination signal 99 that is triggered by a measurement trigger signal 98 (see FIG. 8). The measurements labeled 154 on the other hand represent measurement timings where a measurement is terminated in response to a measurement termination signal 99 that is triggered by a change in the dither signal 53 (see FIG. 8), that is before the measurement trigger signal 98 is generated. The measurement labeled 156 represents a measurement delay that is a function of engine operating conditions.

Figure 12:
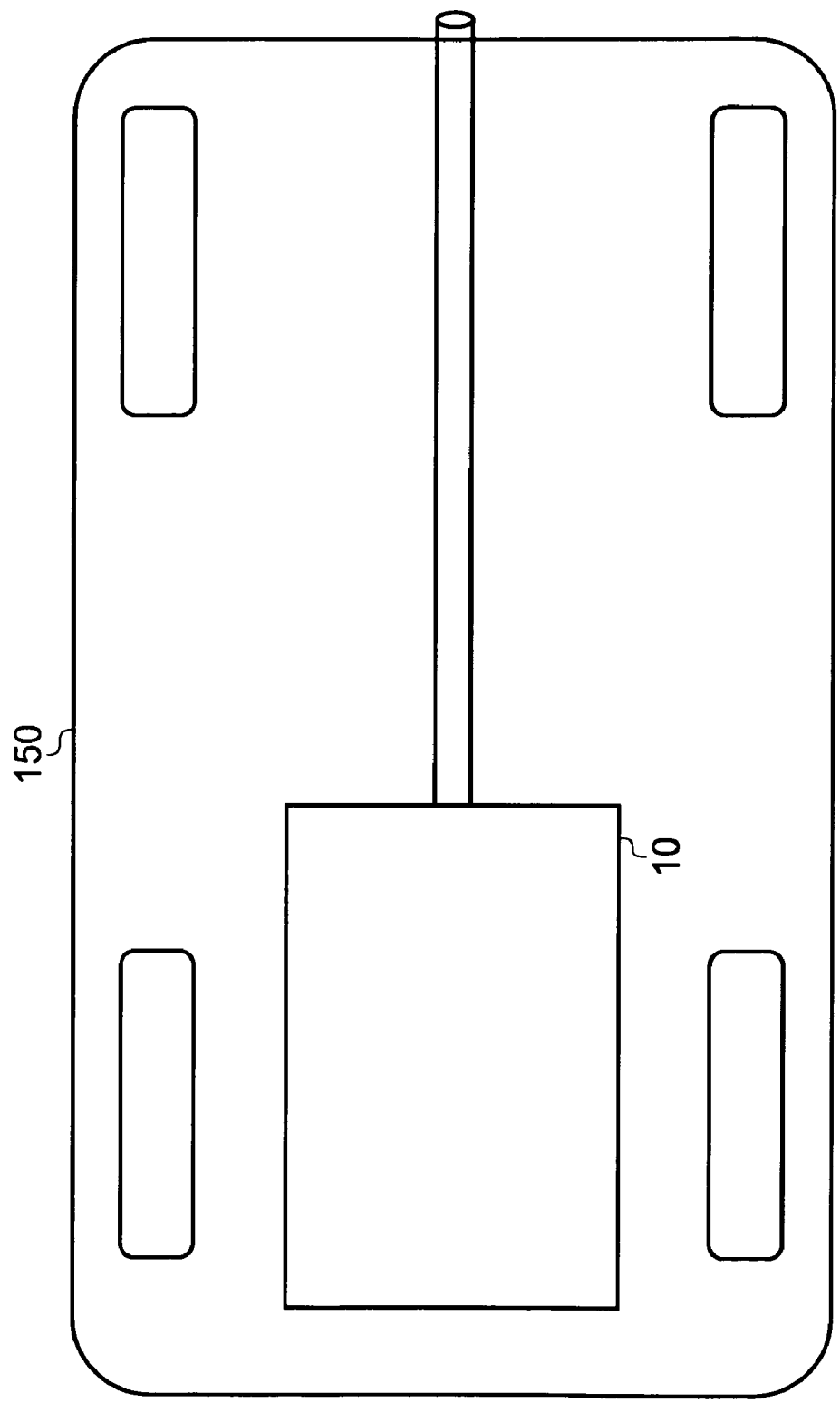
FIG. 12 is a schematic representation of a vehicle.

FIG. 12 is a schematic representation of a vehicle 150 including the engine system 10 described hereinabove.

Figure 13:
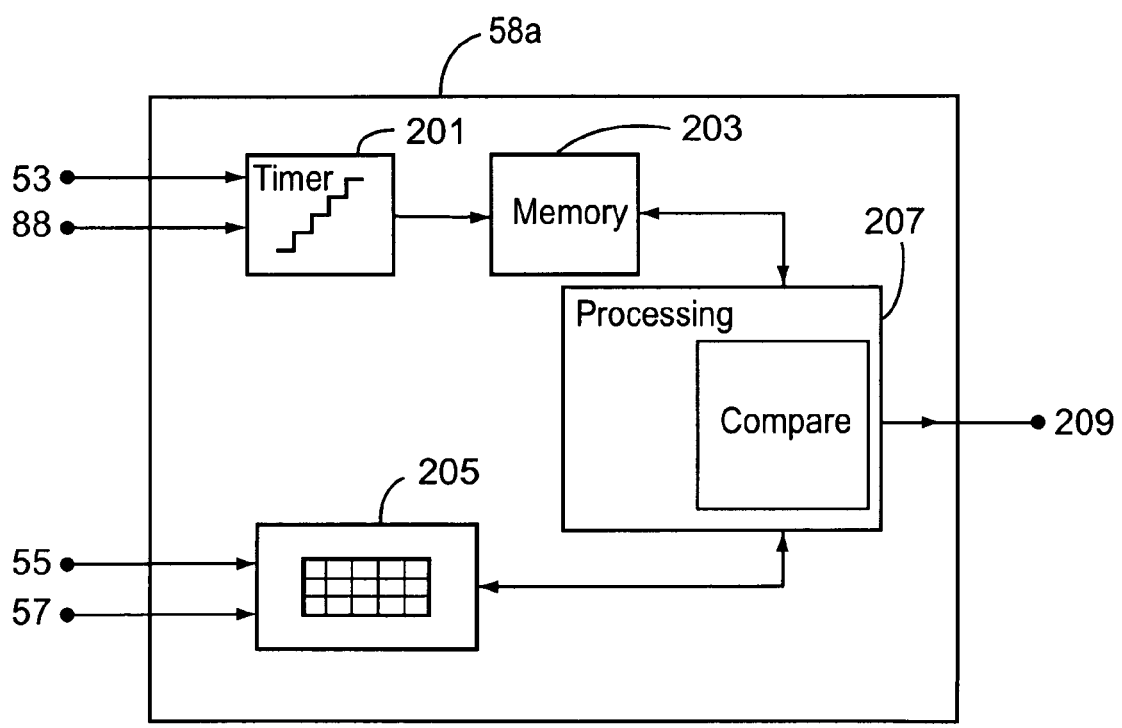
FIG. 13 is a schematic block diagram of an alternative example measurement unit.

FIG. 13 illustrates an alternative embodiment of a measurement unit 58a. The measurement unit 58a may be utilized as part of the oxygen sensor malfunction detection unit 54 including the measurement timing unit 56. The oxygen sensor malfunction detection unit 54, including measurement unit 58a, may implement the methodology illustrated in the flow diagram of FIG. 14 to determine oxygen sensor malfunction.

The measurement unit 58a receives signals representing engine operation parameters such as engine speed 55 and engine load 57. The measurement unit 58a also receives as inputs the determined turning point signal 88 from the measurement timing unit 56 and timing dither signal 53 which at least in this embodiment represents a command signal to begin the at least the monitoring part (303-309) of the diagnostic function illustrated in FIG. 14.

The measurement unit 58a includes programmed logic circuitry for implementing a timer 201, a time threshold table 205 and processing logic 207. The processing logic 207 may, among other things, perform a comparison of times as will be discussed in more detail below. The processing logic 207 outputs a fault signal 209 which may, for example, trigger the engine control unit 40 to illuminate a malfunction indicator light (MIL) in the vehicle or provide a wired or wireless signal to another location indicating the malfunction. The measurement unit 58a also includes memory 203 which stores data received from the timer 201 and is accessible by the processing logic 207. While the memory 203 illustrated in FIG. 13 appears to be the memory specifically dedicated to the measurement unit 58a, the memory 203 may alternatively be formed by memory accessible by other portions of the ECU.

The timer 201 associates a time for receipt of the dither signal 53 and the determined turning point signal 88. The dither signal 53 represents a command signal to initiate a diagnostic function in which the air-fuel ratio is forced to change in a stepwise manner from lean-to-rich or rich-to-lean. The timer 201 determines a response delay time by determining a response time interval between the time associated with dither signal 53 and the time associated with determined turning point signal 88. The timer 201 provides data representing the response time interval to the memory 203. The memory 203 stores data representing the response time interval and other data representing other response time intervals from previous time samples.

The processing logic 207 accesses the response delay time data stored in the memory 203. The processing logic 207 determines those time interval(s) that begin when the dither signal 53 initiates operations to force the air-fuel ratio into a lean-to-rich response and ends when a turning point is determined as indicated by the signal 88. The processing logic 207 also identifies those response time interval(s) which begin when the dither signal 53 begins operations to force the air-fuel ratio into a rich-to-lean response and ends when a turning point is determined as indicated by the signal 88. The processing logic 207 then calculates an average delay time for those response time interval(s) having the forced lean-to-rich response and another average delay time for those response time interval(s) having the forced rich-to-lean response.

The processing logic 207 receives a time threshold for the lean-to-rich response and another time threshold for the rich-to-lean response. Upon request from the processing logic 207 or automatically in a periodic fashion, the timing threshold table 205 provides the lean-to-rich threshold and the rich-to-lean threshold based on received engine parameter signals 55, 57. The processing logic 207 compares the calculated lean-to-rich average delay time with the lean-to-rich threshold and compares the calculated rich-to-lean average delay time with the rich-to-lean threshold. If neither of the thresholds are exceeded, then the processing logic 207 determines that there is no sensor malfunction. On the other hand, if one or the other of the thresholds is exceeded, the processing logic 207 determines a malfunction and outputs a fault signal 209. Alternatively, the processing logic 207 may be programmed to only determine a malfunction if both of the lean-to-rich and rich-to-lean thresholds are exceeded.

Figure 14:
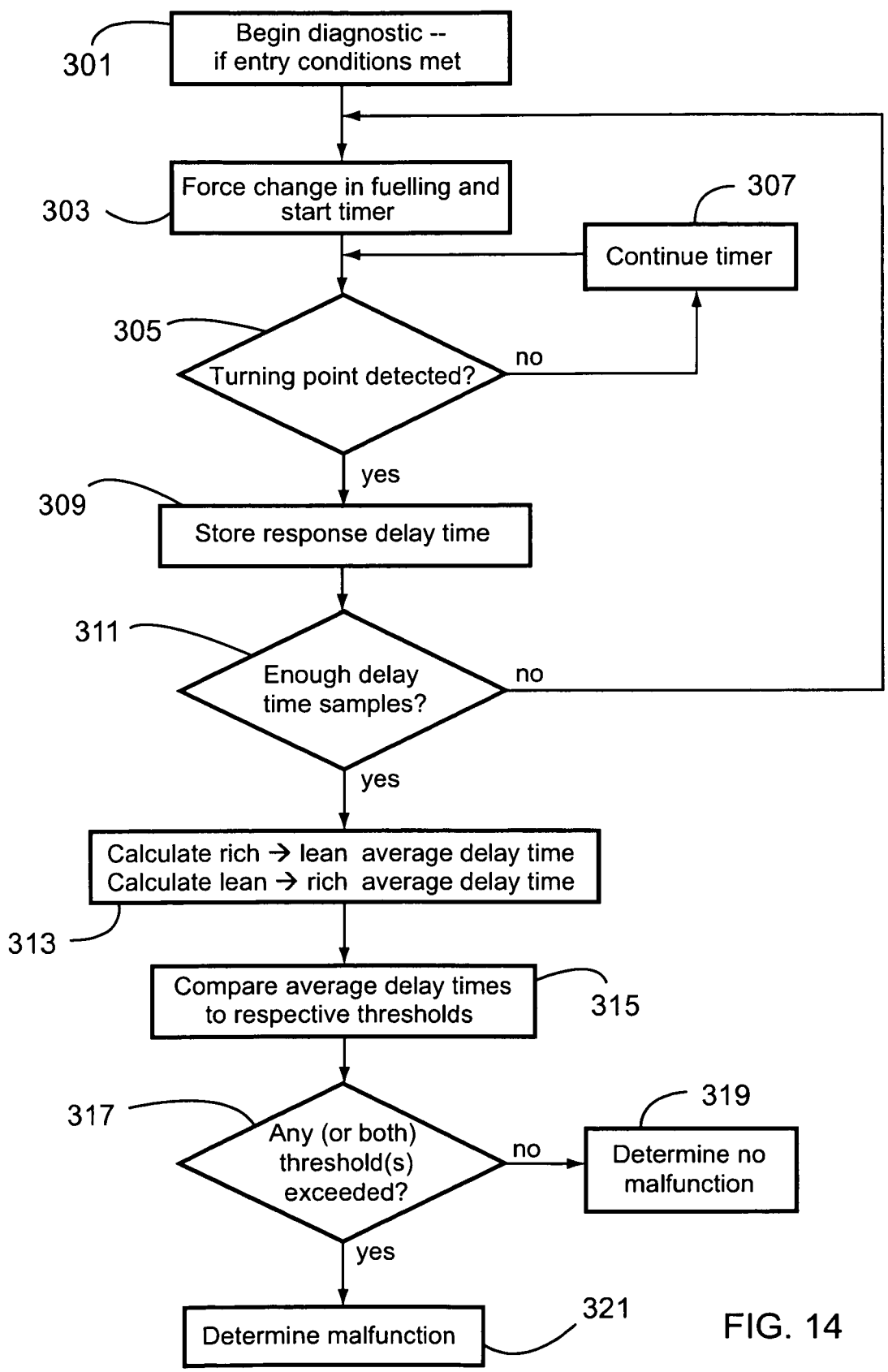
FIG. 14 is a flow diagram illustrating example operation of an engine control unit including the measurement unit illustrated in FIG. 13.

FIG. 14 illustrates a flow diagram illustrating a diagnostic function test that may be implemented via the oxygen sensor malfunction detection unit 54 having the measurement unit 58a. The diagnostic begins in step 301 if certain entry conditions are met. These entry conditions may be, for example, that one or more of the engine speed, time after start of the engine, and/or engine coolant temperature are within predetermined ranges. Assuming that the entry conditions are met, the ECU 40 issues a dither signal 53 to force the air-fuel ratio to change in a stepwise manner in step 303. For example, the dither signal 53 will initiate operations to force a change in fueling via the fuel injectors 28 so that the air-fuel ratio will change from lean-to-rich or from rich-to-lean. The timer 201 of the measurement unit 58a receives the dither signal 53 and starts the count of the timer 201. The timer continues to run in step 307 until a turning point is detected in step 305. The measurement timing unit 56 determines the turning point of a signal from, for example, the UHEGO sensor 48 or HEGO sensor 52 in the manner described above. (See, e.g., the above description associated with FIGS. 3-6).

The memory 203 stores the response delay time of the response time interval beginning at the time that the diagnostic function operations are initiated by the dither signal 53 and ending at the time that the turning point of the sensor signal is determined in step 309. The processing logic 207 then determines whether enough sample(s) of the response time interval have been obtained in step 311. If not, step 303-309 will be repeated in order to obtain additional response time interval(s). The number of samples may be as few as one. If more samples are needed, the dither signal 53 will alternately drive the air-fuel ratio between a rich-to-lean response and a lean-to-rich response. For example, if the first time that steps 303-309 are performed involves the air-fuel ratio being driven from lean-to-rich, then the next time steps 303-309 are performed will involve a rich-to-lean response, and then back again to a lean-to-rich response. The forced change in fueling in step 303 therefore toggles between a rich-to-lean response and a lean-to-rich response. Consecutive samples of response time intervals will involve different rich/lean responses.

The processing logic 207 calculates an average delay time for those samples of response time intervals having a rich-to-lean response in step 313. The processing logic 207 also calculates an average delay time for those samples of response time intervals having a lean-to-rich response in step 313. Again, the number of samples of the response time interval may be merely a single sample thereby making the average delay time equal to the delay time of the single response time interval determined for the rich-to-lean response or for the lean-to-rich response.

The processing logic 207 then compares the average delay time for the rich-to-lean response time intervals to a time threshold received from time threshold table 205, and compares the average delay time for the lean-to-rich response time intervals to another time threshold received from the time threshold table 205 in step 315. The thresholds are determined by the threshold table 205 depending on the engine speed and engine load parameters 55, 57. If the processing logic 207 determines that at least one of the thresholds is exceeded by a respective average time delay, then the processing logic 207 determines that the sensor has a malfunction in step 321. On the other hand, if none of the thresholds are exceeded, the processing logic 207 determines that there is no sensor malfunction in step 319. The processing logic 207 can determine a malfunction in step 321 only if both of the rich-to-lean and lean-to-rich thresholds are exceeded. Alternatively, the processing logic 207 can determine a malfunction in step 321 if only the rich-to-lean threshold is exceeded by the average delay time of the rich-to-lean response time intervals alone or if the lean-to-rich time threshold is exceeded by the average delay time of the lean-to-rich response time intervals alone.

There has been described an internal combustion engine that includes an exhaust system, an oxygen sensor in the exhaust system and a sensor malfunction monitor. The sensor malfunction monitor determines a timing for a turning point of a signal from a sensor and then uses this to determine a period for measuring a rate of change of a signal from the sensor, and can thereby detects a malfunction when a rate of change of the signal exceeds or falls below a threshold. Alternatively, the determined timing for a turning point of a signal from a sensor may be utilized to determine the end point of a time interval which starts when a diagnostic function forcibly changes the engine's air-fuel ratio. This time interval can be compared to a time threshold to determine a malfunction of the sensor if the time interval exceeds the time threshold. Multiple samples of the time intervals when the diagnostic function forces the air-fuel ratio to change from lean-to-rich or from rich-to-lean may be averaged together to determine an average time that is compared to a lean-to-rich or rich-to-lean time threshold for determining sensor malfunction.

Although the embodiments above have been described in considerable detail, numerous variations and modifications will become apparent to those skilled in the art once the above disclosure is fully appreciated. It is intended that the following claims be interpreted to embrace all such variations and modifications as well as their equivalents.

What is claimed is:

1. A sensor malfunction monitor for detecting a sensor malfunction, the sensor malfunction monitor being configured to determine a turning point of a lambda signal from an oxygen sensor to determine a measurement timing utilized to verify the operation of the oxygen sensor, wherein the turning point is a change in direction of the lambda signal from one of an increasing or decreasing signal to the other of an increasing or decreasing signal.

2. The sensor malfunction monitor of claim 1, comprising a turning point detector configured to determine a potential turning point from changes in two or more consecutive sensor signal samples.

3. The sensor malfunction monitor of claim 2, comprising a delay logic including a timer connected to the turning point detector and configured to be reset in response to detection of a potential turning point, whereby a turning point is determined to have been reached in response to the timer timing a delay period since a last reset.

4. The sensor malfunction monitor of claim 3, wherein the delay period is dynamically determined based on engine operating parameters.

5. The sensor malfunction monitor of claim 3, comprising measurement hold logic connected to the delay logic and configured to trigger a sensor measurement following a hold period.

6. The sensor malfunction monitor of claim 5, wherein the hold period is dynamically determined based on engine operating parameters.

7. The sensor malfunction monitor of claim 1, wherein the oxygen sensor is an internal combustion system oxygen sensor.

8. The sensor malfunction monitor of claim 1, wherein the oxygen sensor is a UHEGO sensor.

9. The sensor malfunction monitor of claim 1 wherein the monitor is configured to detect a malfunction of the oxygen sensor when a rate of change of the lambda signal is outside predetermined values.

10. An engine management system for an internal combustion engine, the engine management system comprising: a sensor malfunction monitor configured to detect an asymmetric malfunction manifested in a lambda signal output by an oxygen sensor in an exhaust system of the internal combustion engine, the sensor malfunction monitor being configured to determine a turning point of the lambda signal from the oxygen sensor to determine a measurement timing for verifying the operation of the oxygen sensor, wherein the turning point is a change in direction of the lambda signal from one of an increasing or decreasing signal to the other of an increasing or decreasing signal.

11. The engine management system of claim 10, wherein the sensor malfunction monitor is configured to detect a malfunction of the oxygen sensor when a rate of change of the lambda signal is outside predetermined values.

12. An internal combustion engine system comprising:
an internal combustion engine,
an exhaust system,
an oxygen sensor in the exhaust system, and
a sensor malfunction monitor, the sensor malfunction monitor being configured to determine a turning point of a lambda signal from the oxygen sensor to determine a measurement timing and being configured to verify the operation of the oxygen sensor based on the measurement timing, wherein the turning point is a change in direction of the lambda signal from one of an increasing or decreasing signal to the other of an increasing or decreasing signal.

13. A method of detecting a sensor malfunction, the method comprising:
measuring a rate of change of a lambda signal from an oxygen sensor;
detecting a turning point of the lambda signal, the turning point being a change in direction of the lambda signal from one of an increasing or decreasing signal to the other of an increasing or decreasing signal;
determining a measurement timing based on the turning point; and
verifying the operation of the oxygen sensor based on the measurement timing.

14. The method of claim 13, comprising determining a potential turning point from changes in two or more consecutive sensor signal samples.

15. The method of claim 14, comprising resetting a timer in response to detection of a potential turning point, whereby a turning point is determined to have been reached in response to the timer timing a delay period since a last reset.

16. The method of claim 15, wherein the delay period is dynamically determined based on engine operating parameters.

17. The method of claim 15, comprising triggering a sensor measurement following a hold period.

18. The method of claim 17, wherein the hold period is dynamically determined based on engine operating parameters.

19. The method of claim 13, comprising smoothing the signal and detecting a detecting a turning point of the smoothed signal.

20. The method of claim 13, wherein the oxygen sensor is an internal combustion system oxygen sensor.

21. The method of claim 20, wherein the oxygen sensor is a UHEGO sensor.

22. The method of claim 13, comprising detecting a malfunction of the oxygen sensor when a rate of change of the lambda signal is outside predetermined values.

23. A sensor malfunction monitor comprising:
a turning point detector that detects a turning point of a lambda signal from an oxygen sensor of an engine, wherein the turning point is a change in direction of the lambda signal from one of an increasing or decreasing signal to the other of an increasing or decreasing signal;
a timer that determines at least one time interval having a start time point defined when operation is begun to force an air-fuel ratio of the engine to change and an end time point defined when the turning point is detected by the turning point detector; and
processing logic that determines a sensor malfunction based on the determined time interval.

24. The sensor malfunction monitor of claim 23, wherein the processing logic determines the sensor malfunction by comparing the time interval to a time threshold and determining that the time interval exceeds the time threshold.

25. The sensor malfunction monitor of claim 24, wherein the time threshold is dynamically determined based on at least one engine operating parameter.

26. The sensor malfunction monitor of claim 23, wherein the start time point defined when operation is begun to force the air-fuel ratio of the engine to change is a time point at which operation is begun to force the air-fuel ratio of the engine to change from rich-to-lean or from lean-to-rich.

27. The sensor malfunction monitor of claim 23, wherein the timer determines a plurality of time intervals each having a start time point when operation is begun to force the air-fuel ratio of the engine to change and an end time point when a turning point is detected by the turning point detector, and the processing logic calculates an average time of the plurality of time intervals and compares the calculated average time to a time threshold in order to determine sensor malfunction.

28. The sensor malfunction monitor of claim 23, wherein the timer determines a plurality of time intervals that each have a start time point when operation is begun to force the air-fuel ratio of the engine to change from lean-to-rich and an end time point when a turning point is detected by the turning point detector, and the processing logic calculates an average time of said plurality of time intervals and compares the calculated average time to a time threshold in order to determine sensor malfunction.

29. The sensor malfunction monitor of claim 23, wherein the timer determines a plurality of time intervals that each have a start time point when operation is begun to force the air-fuel ratio of the engine to change from rich-to-lean and an end time point when a turning point is detected by the turning point detector, and the processing logic calculates an average time of said plurality of time intervals and compares the calculated average time to a time threshold in order to determine sensor malfunction.

30. The sensor malfunction monitor of claim 27, wherein:
the timer determines a first set of time intervals that each have a start time point when operation is begun to force the air-fuel ratio of the engine to change from lean-to-rich and an end time point when a turning point is detected by the turning point detector and a second set of time intervals that each have a start time point when operation is begun to force the air-fuel ratio of the engine to change from rich-to-lean and an end time point when a turning point is detected by the turning point detector; and
the processing logic calculates an average time of the first set of time intervals and an average time of the second set of time intervals.

31. The sensor malfunction monitor of claim 30, wherein the average time of the first set of time intervals is compared to a first threshold and the average time of the second set of the time intervals is compared to a second threshold.

32. The sensor malfunction monitor of claim 31, wherein the processing logic determines the sensor malfunction when either the average time of the first set of time intervals exceeds the first threshold or the average time of the second set of the time intervals exceeds the second threshold.

33. The sensor malfunction monitor of claim 31, wherein the processing logic determines the sensor malfunction when both the average time of the first set of time intervals exceeds the first threshold and the average time of the second set of the time intervals exceeds the second threshold.

34. A sensor malfunction monitor for detecting a sensor malfunction, the sensor malfunction monitor being configured to:
determine a turning point of a lambda signal from an oxygen sensor of an engine;
determine at least one time interval having a start time at which operation is begun to force an air-fuel ratio of the engine to change from rich-to-lean or lean-to-rich and having an end time at which the turning point is determined; and
determine a sensor malfunction based on the determined time interval,
wherein the turning point is a change in direction of the lambda signal from one of an increasing or decreasing signal to the other of an increasing or decreasing signal.

35. The sensor malfunction monitor of claim 34, comprising a turning point detector configured to determine a potential turning point from changes in two or more consecutive sensor signal samples.

36. The sensor malfunction monitor of claim 35, comprising a delay logic including a timer connected to the turning point detector and configured to be reset in response to detection of a potential turning point, whereby a turning point is determined to have been reached in response to the timer timing a delay period since a last reset.

37. The sensor malfunction monitor of claim 36, wherein the delay period is dynamically determined based on engine operating parameters.

38. The sensor malfunction monitor of claim 34, wherein the oxygen sensor is an internal combustion system oxygen sensor.

39. The sensor malfunction monitor of claim 38, wherein the oxygen sensor is a UHEGO sensor.

40. The sensor malfunction monitor of claim 34, wherein the sensor malfunction is determined based on the determined time interval includes comparing the time interval to a time threshold and determining that the time interval exceeds the time threshold.

41. The sensor malfunction monitor of claim 34, wherein the malfunction monitor is further configured to: determine a first set of a plurality of time intervals each having a start time at which operation is begun to force the air-fuel ratio of the engine to change from lean-to-rich; determine a second set of a plurality of time intervals each having a start time at which operation is begun to force the air-fuel ratio of the engine to change from rich-to-lean; and calculating a first average time of the first set of the plurality of time intervals and a second average time of the second set of the plurality of time intervals.

42. The sensor malfunction monitor of claim 41, wherein the malfunction monitor is further configured to: compare the first average time to a first threshold and compare the second average time to the second threshold, and determine the sensor malfunction if either the first average time exceeds the first threshold or the second average time exceeds the second threshold.

43. The sensor malfunction monitor of claim 41, wherein the malfunction monitor is further configured to: compare the first average time to a first threshold and compare the second average time to the second threshold, and determine the sensor malfunction if both the first average time exceeds the first threshold and the second average time exceeds the second threshold.

44. A method of detecting sensor malfunction comprising:
detecting a turning point of a lambda signal from an oxygen sensor of an engine, the turning point being a change in direction of the lambda signal from one of an increasing or decreasing signal to the other of an increasing or decreasing signal;
determining at least one time interval that starts when operation is begun to force an air-fuel ratio of the engine to change from lean-to-rich or from rich-to-lean and that ends when the turning point is detected; and determining a sensor malfunction based on the determined time interval.

45. The method of claim 44, further comprising:
determining a set of a plurality of time intervals each of which starts when operations are begun to force the air-fuel ratio of the engine to change from lean-to-rich and which ends when a turning point is detected;
calculating an average time of the set of the plurality of time intervals; and
determining the sensor malfunction when the average time exceeds a time threshold.

46. The method of claim 44, further comprising:
determining a set of a plurality of time intervals each of which starts when operations are begun to force the air-fuel ratio of the engine to change from rich-to-lean and which ends when a turning point is detected;
calculating an average time of the set of the plurality of time intervals; and
determining the sensor malfunction when the average time exceeds a time threshold.

47. The method of claim 44, further comprising:
determining a first set of a plurality of time intervals each of which starts when operations are begun to force the air-fuel ratio of the engine to change from lean-to-rich and which ends when a turning point is detected;
calculating a first average time of the first set of the plurality of time intervals;
determining a second set of a plurality of time intervals each of which starts when operations are begun to force the air-fuel ratio of the engine to change from rich-to-lean and which ends when a turning point is detected;
calculating a second average time of the second set of the plurality of time intervals; and
determining the sensor malfunction when the first average time exceeds the first threshold and the second average time exceeds the second threshold.

48. The method of claim 44, wherein the sensor malfunction is determined when the determined time interval exceeds a time threshold.

49. The method of claim 48, wherein the time threshold is dynamically determined based on engine operating parameters.

50. The sensor malfunction monitor of claim 1, wherein the measurement timing is determined as a time period beginning when operation is begun to force the lambda signal to change and ending when the turning point is determined, the operation of the oxygen sensor being verified based on the measurement timing.

51. The engine management system of claim 10, wherein the measurement timing is determined as a time period beginning when operation is begun to force the lambda signal to change and ending when the turning point is determined, the operation of the oxygen sensor being verified based on the measurement timing.

52. An internal combustion engine system of claim 12, wherein the measurement timing is determined as a time period beginning when operation is begun to force the lambda signal to change and ending when the turning point is determined, the operation of the oxygen sensor being verified based on the measurement timing.

53. A method of claim 13, wherein the measurement timing is determined as a time period beginning when operation is begun to force the lambda signal to change and ending when the turning point is determined, the operation of the oxygen sensor being verified based on the measurement timing.

* * * * *